(12) United States Patent
Osman et al.

(10) Patent No.: US 9,731,085 B2
(45) Date of Patent: Aug. 15, 2017

(54) CARTRIDGE ASSEMBLY HAVING SHARED FASTENING MEANS AND DRUG DELIVERY DEVICE

(75) Inventors: Thomas Frederick Osman, Leamington Spa (GB); Richard James Vincent Avery, Chipping Campden (GB); Joseph Butler, Rugby (GB); Aled Meredydd James, West Midlands (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 255 days.

(21) Appl. No.: 13/642,691

(22) PCT Filed: Apr. 21, 2011

(86) PCT No.: PCT/EP2011/056473
§ 371 (c)(1),
(2), (4) Date: Jan. 18, 2013

(87) PCT Pub. No.: WO2011/131776
PCT Pub. Date: Oct. 27, 2011

(65) Prior Publication Data
US 2013/0211327 A1    Aug. 15, 2013

Related U.S. Application Data

(60) Provisional application No. 61/327,274, filed on Apr. 23, 2010.

(30) Foreign Application Priority Data

Jul. 29, 2010 (EP) .................................... 10171163

(51) Int. Cl.
*A61M 5/50* (2006.01)
*A61M 5/24* (2006.01)
(Continued)

(52) U.S. Cl.
CPC ............ *A61M 5/5086* (2013.01); *A61M 5/24* (2013.01); *A61M 5/3135* (2013.01);
(Continued)

(58) Field of Classification Search
CPC .. A61M 2005/2407; A61M 2005/2433; A61M 2005/2437; A61M 2005/2488;
(Continued)

(56) References Cited

U.S. PATENT DOCUMENTS 4,968,299 A * 11/1990 Ahlstrand ........... A61M 5/2448
604/191
5,514,097 A * 5/1996 Knauer ................... A61M 5/20
604/136

(Continued)

FOREIGN PATENT DOCUMENTS

CN    101489607 A    7/2009
WO    2008/009646 A1    1/2008
(Continued)

OTHER PUBLICATIONS

International Preliminary Report on Patentability for Int. App. No. PCT/EP2011/056473, mailed Nov. 1, 2012.
(Continued)

*Primary Examiner* — Quynh-Nhu H Vu
(74) *Attorney, Agent, or Firm* — McDonnell Boehnen Hulbert & Berghoff LLP

(57) ABSTRACT

A cartridge assembly (200) having a shared fastening features for use with a drug delivery device (202). The cartridge assembly includes a cartridge holder (204), a drug cartridge (206), and a connector (208). The connector may be attached to the drug cartridge. The cartridge assembly further includes a fastening means (210, 212) for fastening to a drug delivery device, and this fastening means is shared between the cartridge holder and the cartridge or between the car-
(Continued)

tridge holder and the connector. The drug delivery device may be a reusable drug delivery device or a disposable drug delivery device.

8 Claims, 11 Drawing Sheets

(51) Int. Cl.
  *A61M 5/31* (2006.01)
  *A61M 5/315* (2006.01)
(52) U.S. Cl.
  CPC . *A61M 5/31551* (2013.01); *A61M 2005/2407* (2013.01); *A61M 2005/2433* (2013.01); *A61M 2005/2488* (2013.01); *A61M 2205/6045* (2013.01)
(58) Field of Classification Search
  CPC ...... A61M 2005/2492; A61M 2005/24; A61M 2005/2403; A61M 5/3135; A61M 5/31551; A61M 2205/6045; A61M 39/00; A61M 39/10; A61M 2039/1033; A61M 2039/1038; A61M 2039/1061; A61M 2039/1077; A61M 16/0816
  USPC ................................ 604/187, 197, 232, 240
  See application file for complete search history.

(56) References Cited

U.S. PATENT DOCUMENTS

| | | | | |
|---|---|---|---|---|
| 6,471,677 | B2* | 10/2002 | Domici, Jr. | 604/198 |
| 6,582,399 | B1* | 6/2003 | Smith et al. | 604/152 |
| 6,582,408 | B1* | 6/2003 | Buch-Rasmussen | A61M 5/24 604/187 |
| 6,648,859 | B2* | 11/2003 | Bitdinger et al. | 604/232 |
| 7,976,514 | B2* | 7/2011 | Abry | A61M 5/20 604/110 |
| 2001/0010455 | A1* | 8/2001 | Brotto | H02J 7/0004 320/106 |
| 2003/0139705 | A1* | 7/2003 | Larsen | A61M 5/326 604/198 |
| 2007/0100294 | A1* | 5/2007 | Sugita | A61M 5/3129 604/241 |
| 2008/0172001 | A1* | 7/2008 | Reynolds | A61J 1/2089 604/232 |
| 2008/0208142 | A1* | 8/2008 | Moller | A61M 5/31541 604/208 |
| 2010/0280461 | A1* | 11/2010 | Forstreuter | A61M 5/31515 604/228 |
| 2011/0092917 | A1* | 4/2011 | Wei | A61M 5/24 604/241 |

FOREIGN PATENT DOCUMENTS

| | | |
|---|---|---|
| WO | 2008/025772 A1 | 3/2008 |
| WO | 2008/062025 A1 | 5/2008 |
| WO | 2008074897 A1 | 6/2008 |

OTHER PUBLICATIONS

Form PCT/ISA/220, Notification of Transmittal of the International Search Report and the Written Opinion of the International Search Authority, or the Declaration dated Aug. 3, 2011.

* cited by examiner

CARTRIDGE ASSEMBLY HAVING SHARED FASTENING MEANS AND DRUG DELIVERY DEVICE

This application is a U.S. national phase of International Application No. PCT/EP2011/056473 filed on Apr. 21, 2011, which claims priority to U.S. Provisional Application No. 61/327,274 filed on Apr. 23, 2010 and European Patent Application No. 10171163.8 filed on Jul. 29, 2010, the disclosures of which are incorporated herein by reference in their entirety.

FIELD OF PATENT APPLICATION

The present patent application is generally directed to reservoirs, particularly reservoirs containing a medicament. More particularly, the present application is generally directed to a cartridge assembly having a shared fastening means, the cartridge assembly being for use with a drug delivery device, so as to prevent unwanted reservoir cross use. As just one example, such medicament reservoirs may comprise an ampoule, a cartridge, a vial, or a pouch, and may be used with a medical delivery device. Exemplary medical delivery devices include, but are not limited to syringes, pen type injection syringes, pumps, inhalers, or other similar injection or infusing devices that require at least one reservoir containing at least one medicament.

BACKGROUND

Medicament reservoirs such as ampoules, cartridges, or vials are generally known. Such reservoirs are especially used for medicaments that may be self administered by a patient. For example, with respect to insulin, a patient suffering from diabetes may require a certain amount of insulin to either be injected via a pen type injection syringe or infused via a pump. With respect to certain known reusable pen type drug delivery devices, a patient loads a cartridge containing the insulin into a proximal end of a cartridge holder. After the cartridge has been correctly loaded, the user may then be called upon to select a dose of medicament. Multiple doses may be dosed from the cartridge. Where the drug delivery device comprises a reusable device, once the cartridge is empty, the cartridge holder is disconnected from the drug delivery device and the empty cartridge is removed and replaced with a new cartridge. Most suppliers of such cartridges recommend that the user dispose of the empty cartridges properly. Where the drug delivery device comprises a disposable device, once the cartridge is empty, the user is recommended to dispose of the entire device.

Such known self administration systems requiring the removal and reloading of empty cartridges have certain limitations. For example, in certain generally known systems, a user simply loads a new cartridge into the delivery system without the drug delivery device or without the cartridge having a mechanism of preventing cross use of an incorrect cartridge. That is, the drug delivery device does not have a mechanism for determining if the medicament contained in the cartridge is indeed the correct type of medicament to be administered by the patient. Alternatively, certain known drug delivery devices do not present a mechanism for determining if the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short acting insulin in lieu of a long acting insulin could result in injury or even death.

Some drug delivery devices or systems may use a color coding scheme to assist a user or care giver in selecting the correct cartridge to be used with a drug delivery device. However, such color coding schemes pose challenges to certain users, especially those users suffering from poor eyesight or color blindness: a situation that can be quite prevalent in patients suffering from diabetes.

Another concern that may arise with such disposable cartridges is that these cartridges are manufactured in essentially standard sizes and manufactured to comply with certain recognized local and international standards. Consequently, such cartridges are typically supplied in standard sized cartridges (e.g., 3 ml cartridges). Therefore, there may be a variety of cartridges supplied by a number of different suppliers and containing a different medicament but they may fit a single drug delivery device. As just one example, a first cartridge containing a first medicament from a first supplier may fit a medical delivery device provided by a second supplier. As such, a user might be able to load and then dispense an incorrect medicament (such as a rapid or basal type of insulin) into a drug delivery device without being aware that the medical delivery device was perhaps neither designed nor intended to be used with such a cartridge.

WO2008009646 shows a medical delivery system having a container and a dosing assembly, wherein one of the container and the dosing assembly comprises a rotatable element adapted to engage the other one of the container and the dosing assembly. The rotatable element is temporarily retained rotationally relative to the dosing assembly by means of a knob which engages corresponding knobs in the dosing assembly, whereby the rotatable element may be retained in a predetermined number of positions.

WO2008062025 shows a medical delivery system comprising a container which is adapted to be fastened to a dosing assembly. One of the container and the dosing assembly comprises a rotatable element adapted to cooperate with the other one of the container and the dosing assembly, so as to lock/fasten the container to the dosing assembly.

As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

There is, therefore, a general need to physically dedicate or mechanically code a cartridge to its drug type and design an injection device that accepts or works with the dedication or coded features provided on or with the cartridge so as to prevent unwanted cartridge cross use. Similarly, there is also a general need for a dedicated cartridge that allows the medical delivery device to be used with an authorized cartridge containing a specific medicament while also preventing undesired cartridge cross use.

There is also a general need to provide a dedicated cartridge that is difficult to tamper with so that the cartridge may not be compromised in that the cartridge can be used with an unauthorized drug or drug delivery device. Because such cartridges may be difficult to tamper with, they may also reduce the risk of counterfeiting: i.e., making it more difficult for counterfeiters to provide unregulated counterfeit medicament carrying products.

It is an object of the invention to provide a new cartridge assembly which can be used in a drug delivery device, and a new drug delivery device comprising the new cartridge assembly.

This object is achieved by the cartridge assembly according to claim 1 and the drug delivery device according to claim 17, respectively. Embodiments derive from the dependent claims.

An embodiment of the cartridge assembly comprises a cartridge holder and a cartridge. The cartridge holder is provided with a first fastening feature, and the cartridge is provided with a second fastening feature. The first fastening feature and the second fastening feature are provided as a fastener to connect the cartridge assembly to a drug delivery device. The fastener is thus shared between the cartridge holder and the cartridge or between the cartridge holder and the connector.

SUMMARY

According to an exemplary arrangement, a cartridge assembly includes a cartridge holder, a drug cartridge, and a connector. The connector is attached to the drug cartridge. The cartridge assembly further includes a fastening means for fastening to a drug delivery device, and this fastening means is shared between the cartridge holder and the connector.

In another arrangement, the fastening means is shared between the cartridge holder and the cartridge itself. The cartridge assembly includes a cartridge holder, a drug cartridge, and a fastening means for fastening to a drug delivery device. In this arrangement, the fastening means is shared between the cartridge holder and the cartridge.

Another arrangement comprises a cartridge holder and a connector having a shared fastening means between the cartridge holder and the connector. In this arrangement, the connector has a first sidewall that extends a partial extent of the circumference of the connector. Further, the cartridge holder has a second sidewall that extends a partial extent of the circumference of the holder. When the connector and holder are attached, the connector and holder form a substantially complete ring around a cross section of the holder and connector.

In the following the term "distal end" refers to a part of the cartridge assembly or of a body or housing which is intended to be arranged at a portion of a drug delivery device from which a drug is dispensed. The term "proximal end" refers to a part of the cartridge assembly or of the body or housing which is remote from the distal end. The term "distal direction" refers to a movement in the same direction as a movement from the proximal end towards the distal end, not specifying a point of departure nor an end point, so that the movement may go beyond the distal end. The term "proximal direction" refers to a movement in the direction opposite to the distal direction.

In an embodiment of the cartridge assembly the connector has a first sidewall that extends a partial extent of the circumference of the connector, the cartridge holder has a second sidewall that extends a partial extent of the circumference of the cartridge holder, and the first sidewall and the second sidewall combine to form a complete circumference when the connector and the cartridge holder are attached.

In a further embodiment of the cartridge assembly, protrusions and indentations on the connector and on the cartridge holder are provided as coding features.

In a further embodiment of the cartridge assembly, the first fastening feature and the second fastening feature are adapted to a groove of a drug delivery device, the groove having an ejection channel, the first fastening feature being able to enter the ejection channel and the second fastening feature being prevented from entering the ejection channel.

In a further embodiment of the cartridge assembly, the first fastening feature and the second fastening feature comprise at least two sets of fastening features.

An embodiment of the cartridge assembly comprises a cartridge holder, a drug cartridge, and a connector, wherein the connector is attached to the drug cartridge, and a fastener that fastens to a drug delivery device, wherein the fastener is shared between the cartridge holder and the connector.

In a further embodiment of the cartridge assembly the fastening means comprises a first fastening feature on the cartridge holder and a second fastening feature on the connector.

In a further embodiment of the cartridge assembly the first fastening feature is a protrusion from the cartridge holder and the second fastening feature is a protrusion from the connector.

In a further embodiment of the cartridge assembly the cartridge holder does not connect to the drug delivery device when the cartridge holder is not attached to the drug cartridge having the connector with the second fastening feature.

In a further embodiment of the cartridge assembly the drug delivery device comprises a corresponding fastening feature, wherein the corresponding fastening feature includes a groove having an ejection channel, and during insertion of the cartridge assembly into the drug delivery device, the shared fastening means follows the groove and the second fastening feature acts as a stop feature that prevents the first fastening feature from entering the ejection channel.

In a further embodiment of the cartridge assembly, during an attempted insertion of the cartridge holder into the drug delivery device when the cartridge holder is not attached to the drug cartridge having the connector with the second fastening feature, the first fastening means enters the ejection channel.

In a further embodiment of the cartridge assembly the drug delivery device includes a spring mechanism, wherein the spring mechanism rotates the cartridge assembly toward the ejection channel in order to ensure that a cartridge is rejected if the connector is not fitted.

A further embodiment of the cartridge assembly further comprises a second spring mechanism, wherein the second spring mechanism forces the cartridge assembly in a distal direction in order to ensure that the cartridge is rejected if the connector is not fitted.

In a further embodiment of the cartridge assembly the first and second fastening features together form a pin-type fastening means.

In a further embodiment of the cartridge assembly the first and second fastening features together form a groove.

In a further embodiment of the cartridge assembly the connector comprises a non-rotation feature that prevents relative rotation between the cartridge holder and the connector.

In a further embodiment of the cartridge assembly the connector is fitted around a sidewall of the drug cartridge.

In a further embodiment of the cartridge assembly the connector is fixed around the sidewall by at least one of adhesive and glue.

In a further embodiment of the cartridge assembly the connector is coded to the cartridge holder.

In a further embodiment of the cartridge assembly the fastening means is coded to the drug delivery device.

In a further embodiment of the cartridge assembly the fastening means is coded to the drug delivery device by the position of a stop feature of the fastening means.

In a further embodiment of the cartridge assembly the connector has a circumferential extent of 1 degree to 360 degrees.

In a further embodiment of the cartridge assembly the drug cartridge is a 3 ml drug cartridge.

In a further embodiment of the cartridge assembly the drug delivery device includes a dose setting mechanism, and the cartridge assembly connects to the dose setting mechanism.

In a further embodiment of the cartridge assembly the fastening means comprises 1-4 sets of fastening features.

In a further embodiment of the cartridge assembly the connector has a first sidewall that extends a partial extent of the circumference of the connector, the cartridge holder has a second sidewall that extends a partial extent of the circumference of the holder, and, when the connector and holder are attached, the connector and holder form a substantially complete ring around a cross section of the holder and connector.

In a further embodiment of the cartridge assembly the connector is coded to the holder by an angle of the first sidewall.

In a further embodiment of the cartridge assembly the drug delivery device comprises a reusable drug delivery device.

In a further embodiment of the cartridge assembly the drug delivery device comprises a disposable drug delivery device.

An embodiment of the cartridge assembly comprises a cartridge holder, a cartridge and a fastening means for fastening to a delivery device, and the fastening means is shared between the cartridge holder and the cartridge.

In a further embodiment of the cartridge assembly the cartridge is coded to the holder.

In a further embodiment of the cartridge assembly the fastening means is coded to the delivery device.

In a further embodiment of the cartridge assembly the fastening means comprises a first fastening feature on the cartridge holder and a second fastening feature on the cartridge.

In a further embodiment of the cartridge assembly the first and second fastening features together form a pin-type fastening means.

In a further embodiment of the cartridge assembly the first and second fastening features together form a groove.

In a further embodiment of the cartridge assembly the second fastening feature is formed on the cartridge during molding of the cartridge.

In a further embodiment of the cartridge assembly the delivery device comprises a reusable delivery device.

In a further embodiment of the cartridge assembly the delivery device comprises a disposable delivery device.

An embodiment of the cartridge assembly comprises a cartridge holder, a connector, and a fastener that fastens to a drug delivery device, the fastener is shared between the cartridge holder and the connector, the connector has a first sidewall that extends a partial extent of the circumference of the connector, the cartridge holder has a second sidewall that extends a partial extent of the circumference of the holder, and, when the connector and holder are attached, the connector and holder form a substantially complete ring around a cross section of the holder and connector.

In a further embodiment of the cartridge assembly the connector includes a first fastening feature, and wherein the holder includes a second fastening feature.

In a further embodiment of the cartridge assembly the first fastening feature is located on the first sidewall, and wherein the second fastening feature is located on the second sidewall.

A further embodiment of the cartridge assembly further comprises a drug cartridge.

An embodiment of the cartridge arrangement comprises a cartridge holder, a cartridge positioned within the cartridge holder, and a coding feature, which meshes with a corresponding coding feature provided by the cartridge holder during assembly of the cartridge to the holder and which meshes with a corresponding coding feature provided by a delivery device during an assembly of the cartridge holder to the delivery device.

In a further embodiment of the cartridge assembly the coding feature comprises a radial protrusion.

In a further embodiment of the cartridge assembly the coding feature comprises an indentation.

In a further embodiment of the cartridge assembly the drug delivery device comprises a dose setting mechanism.

An embodiment of the drug delivery device comprises a groove with an ejection channel and a cartridge assembly. The cartridge assembly comprises a cartridge holder, a connector, which is provided to be attached to a cartridge, a first fastening feature of the cartridge holder, and a second fastening feature of the connector. The first fastening feature and the second fastening feature move in the groove when the cartridge holder, provided with a cartridge and the connector, is being attached. The first fastening feature enters the ejection channel during an attempt to attach the cartridge holder when the cartridge holder is not provided with a cartridge and the connector.

A further embodiment of the drug delivery device further comprises a spring mechanism, which rotates the cartridge assembly toward the ejection channel in order to ensure that a cartridge is rejected if the connector is not fitted.

A further embodiment of the drug delivery device further comprises a second spring mechanism, which forces the cartridge assembly along the ejection channel to ensure that the cartridge is rejected if the connector is not fitted.

The term "drug" or "medicament", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy,
wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
H-des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The scope of the invention is defined by the content of the claims. The invention is not limited to specific embodiments but comprises any combination of elements of different embodiments. Moreover, the invention comprises any combination of claims and any combination of features disclosed by the claims.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described in the following detailed description with reference to the drawings, in which.

DETAILED DESCRIPTION

Figure 1A:
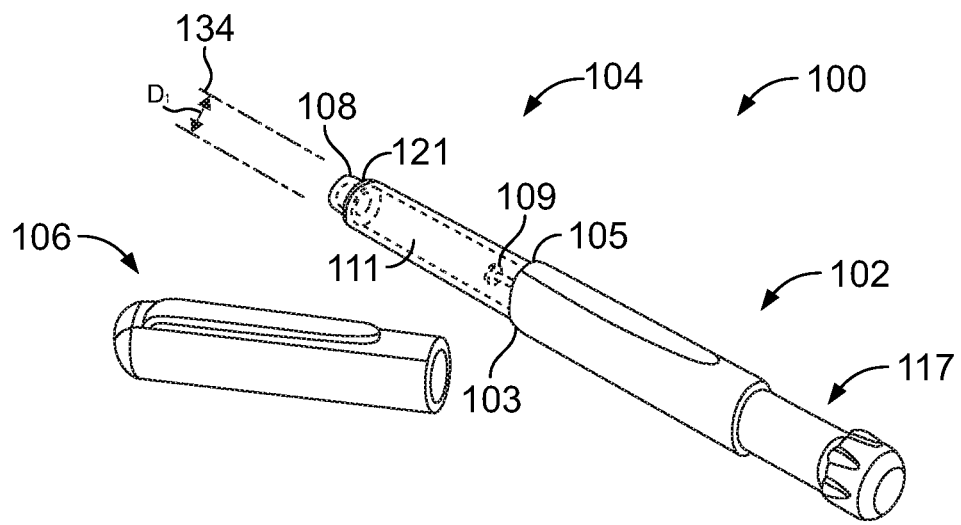
FIG. 1a illustrates an exemplary pen type drug delivery device.

Referring to FIG. 1a, there is shown a drug delivery device 100, which may have the form of a pen. This drug delivery device 100 may comprise a dose setting member 102 comprising a dose setting mechanism, a cartridge holder 104, and a removable cap 106. A proximal end 105 of the cartridge holder 104 and a distal end 103 of the dose setting member 102 are removably secured together. The pen type syringe may comprise a re-usable or a disposable pen type syringe. Where the syringe comprises a re-usable device, the cartridge holder 104 and the dose setting member 102 are removably coupled together. In a disposable device, they are permanently coupled together. In the embodiment according to FIG. 1, the dose setting mechanism comprises a piston rod 109, such as a threaded piston rod 109 that rotates when a dose is injected.

To inject a previously set dose, a double ended needle assembly may be attached to a distal end 108 of the cartridge holder 104. Preferably, the distal end 108 of the cartridge holder 104 comprises a thread 121 (or other suitable connecting mechanism such as a snap lock, snap fit, form fit, or bayonet lock mechanism) so that the needle assembly may be removably attached to the distal end 108 of the cartridge holder 104. When the drug delivery device 100 is not in use, the removable cap 106 can be releasably retained over the cartridge holder 104.

Figure 1B:
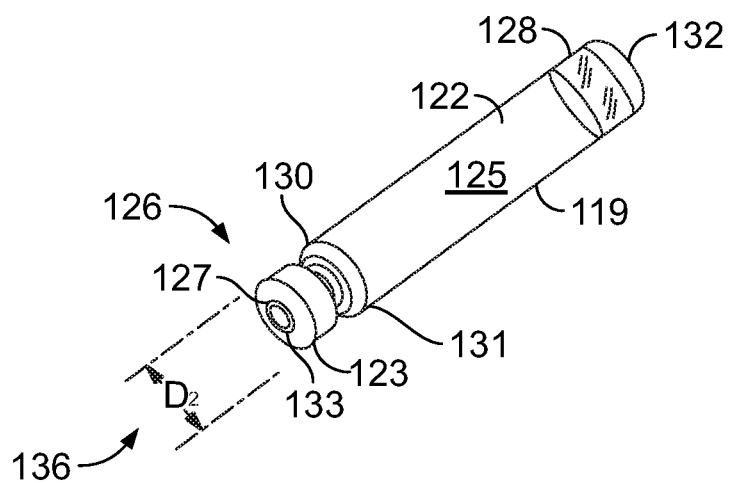
FIG. 1b illustrates an exemplary drug cartridge.

An inner cartridge holder cavity 111 defined by the cartridge holder 104 is dimensioned and configured to securely receive and retain a cartridge 119, such as glass cartridge 119. FIG. 1b illustrates a perspective view of the cartridge 119 that may be used with the drug delivery device 100 illustrated in FIG. 1a. Typically, the cartridge 119 is manufactured of glass and includes a generally tubular barrel 122 extending from a distal end 130 to a proximal end 132.

At the distal end 130, the cartridge 119 may include a smaller diameter neck 126, and this neck 126 projects distally from the shoulder 131 of the barrel 122. Preferably, this smaller diameter neck 126 is provided with a large diameter annular bead 123 and this annular bead 123 extends circumferentially thereabout at the extreme distal end of the neck 126 and defines an opening 127. A pierceable seal or septum 133 may be securely held across the opening 127 by a metallic sleeve or a ferrule.

The medicament 125 is pre-filled into the cartridge 119 and is retained within this cartridge 119, in part, by the pierceable seal or septum 133, a ferrule, and the stopper 128. The stopper 128 is in sliding fluid-tight engagement with the inner tubular wall of the barrel 122. Axially directed forces acting upon the stopper 128 during dose injection or dose administration urges the medication 125 from the cartridge 119 through a double ended needle mounted onto the distal end 130 of the cartridge holder 104 and into the injection site. Such axial forces may be provided by the piston rod 109 working in unison with the dose setting mechanism.

A portion of the cartridge holder 104 defining the cartridge holder cavity 111 is of substantially uniform diameter represented in FIG. 1a by diameter $D_1$ 134. This diameter $D_1$ 134 is preferably slightly greater than the diameter $D_2$ 136 of the cartridge 119. The interior of the cartridge holder 104 includes an inwardly-extending annular portion or stop that is dimensioned to prevent the cartridge 119 from moving within the cartridge holder 104. In this manner, when the cartridge 119 is loaded into the cartridge holder cavity 111 of the cartridge holder 104 and the cartridge holder 104 is then connected to the dose setting member 102, the cartridge 119 will be securely held within the cartridge holder cavity 111.

A number of doses of a medicament 125 may be dispensed from the cartridge 119. Preferably, the cartridge 119 contains a type of medicament 125 that must be administered often, such as one or more times a day. One such medicament 125 is insulin.

The dose setting member 102 comprises a dose setter 117 at the proximal end of the dose setting member 102. In one preferred arrangement, the dose setter 117 is rotated to set a dose. To administer this set dose, the user may attach the needle assembly comprising a double ended needle on the distal end 108 of the cartridge holder 104. In this manner, the needle assembly pierces the seal or septum 133 of the cartridge 119 and is therefore in liquid communication with the medicament 125. The user pushes on the dose setter 117 to inject the set dose. The same dose setting and dose administration procedure is followed until the medicament 125 in the cartridge 119 is expended and then a new cartridge 119 may be loaded in the device. To exchange an empty cartridge 119, the user is called upon to remove the cartridge holder 104 from the dose setting member 102.

In accordance with exemplary embodiments, a cartridge assembly (e.g., a drug cartridge inserted into a cartridge holder or a molded cartridge) includes features (herein referred to as a "fastener", "fastening features" or "fastening means") for fastening the assembly to a drug delivery device. In accordance with certain aspects of the embodiments, the fastening features are shared between the cartridge holder and the cartridge. In a preferred embodiment, a connector may be attached to the cartridge, and the fastening means is shared between the cartridge holder and the connector that is attached to the drug cartridge. Beneficially, in order to connect the cartridge holder having a portion of the shared fastening means to a drug delivery device, the cartridge holder is connected to a connector that has the other portion of the shared fastening means. Alternatively, in other embodiments, the cartridge itself may include the shared fastening means. In such a case, in order to be installed, the holder may be connected to a cartridge having the other portion of the shared fastening means.

In an exemplary embodiment, the shared fastening means of the cartridge assembly is coded to the drug delivery device. That is, the cartridge assembly can only connect to the device if the device has coding features complementary to the coding features (e.g., coded shared fastening means) of the cartridge assembly. Beneficially, if the coding features of the cartridge assembly and the device (e.g., dose setting mechanism) are not matched (i.e., complementary), the two parts cannot be assembled together. Thus, a coded cartridge assembly may only be connected with intended delivery devices and vice versa. Preferably, the coding features of a cartridge assembly only match those of a device when the cartridge assembly is intended to be used by that particular device (or devices). Thus, when attempting to connect an incorrect cartridge assembly (e.g., with an incorrect drug), the user may be alerted at an early stage of assembly that the cartridge assembly is not intended for that particular drug delivery device.

Therefore, in accordance with embodiments, in order that the coded cartridge holder can be connected to a device, two factors must be met: (i) the holder is attached to a connector, so that the assembly includes the shared fastening means of the holder and connector, and (ii) the coding features of the assembly match the coding features of the device.

Further, in an exemplary embodiment, the connector with the shared fastening means is coded to the cartridge holder. Thus, a connector may only be connected with an intended cartridge holder and vice versa. Similarly, in the embodiment where the cartridge itself includes the shared fastening means, the cartridge may be coded to the cartridge holder.

Figure 2:
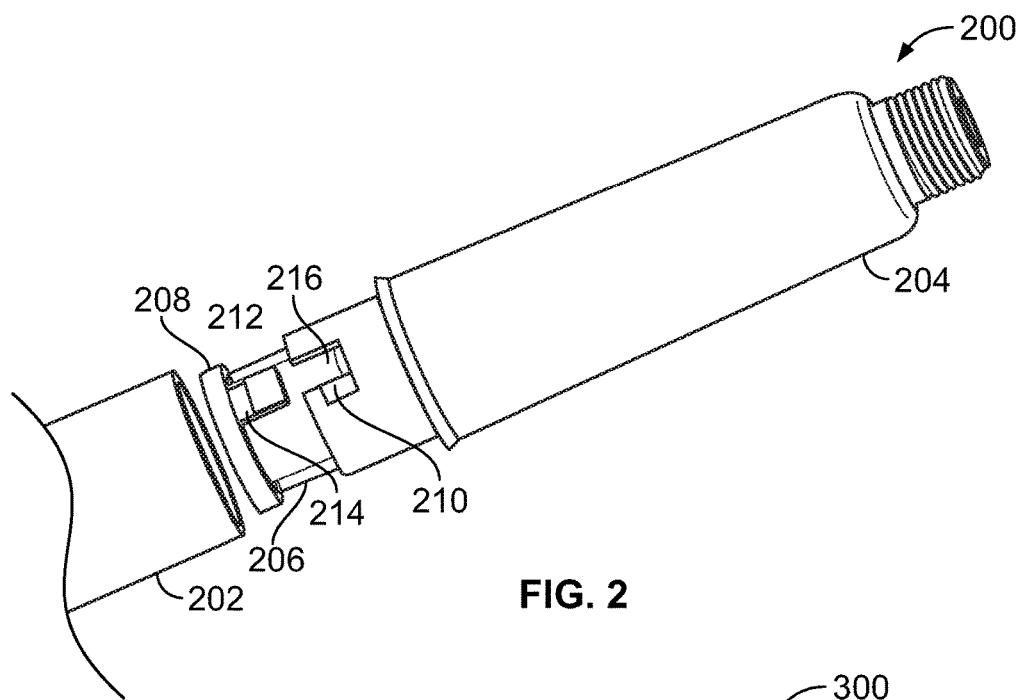
FIG. 2 is a perspective view of an exemplary cartridge assembly and a distal end of an exemplary drug delivery device.
Figure 3:
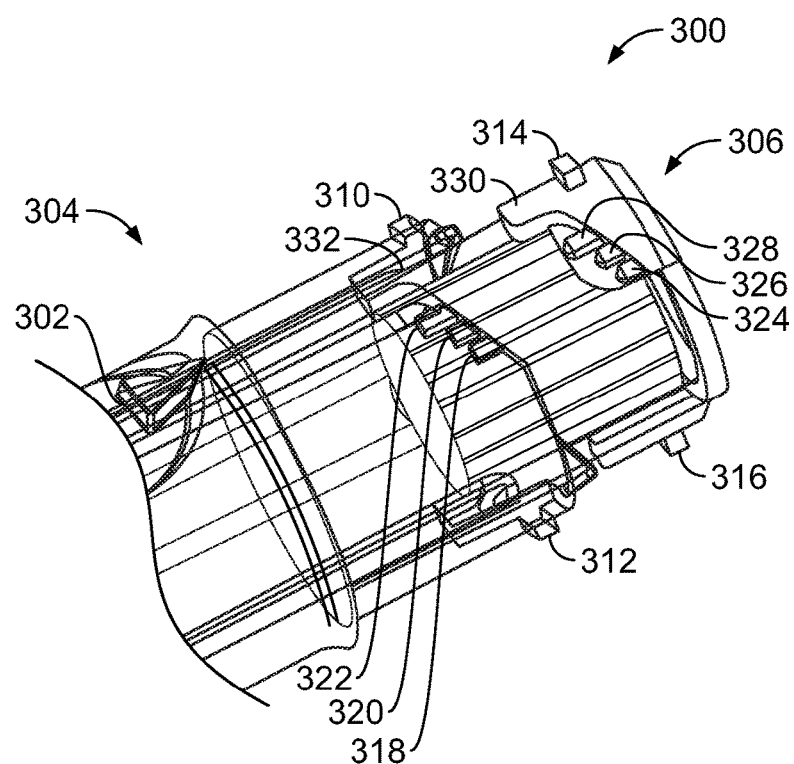
FIG. 3 is a perspective view of an exemplary cartridge assembly.
Figure 4:
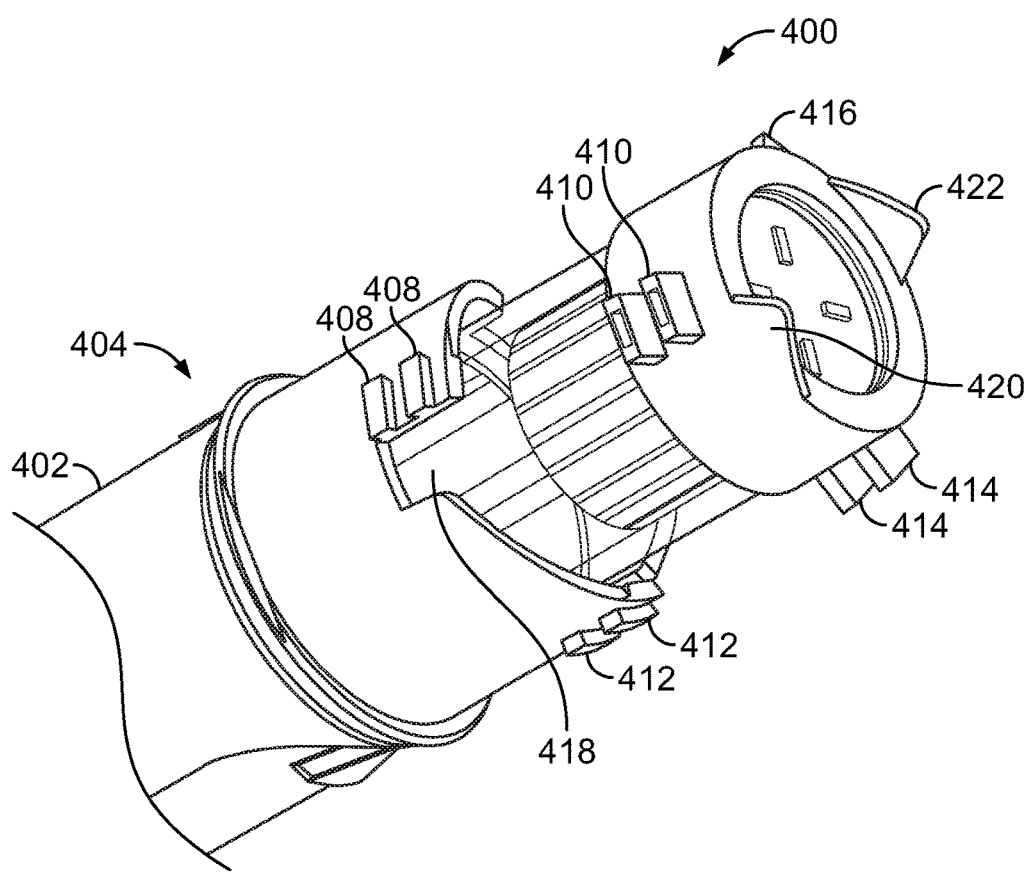
FIG. 4 is a perspective view of an exemplary cartridge assembly.

The cartridge assembly having a shared fastening means (i.e., shared fastening features) may take a variety of different forms. Examples of possible cartridge assemblies are shown in FIGS. 2-4. These Figures depict possible examples of cartridge assemblies where a connector and cartridge holder share the fastening means. In these examples, the connector is attached to a drug cartridge, and then the drug cartridge is inserted into the cartridge holder. However, it should be understood that the cartridge itself may include the shared fastening means. If the cartridge itself includes the shared fastening features, a connector is not necessary. Rather, the shared fastening means may, for example, be formed in the cartridge glass or molding or included on the label.

FIG. 2 depicts an exemplary cartridge assembly 200 that is connectable to a drug delivery device 202. Cartridge assembly 200 includes a cartridge holder 204, a cartridge 206 inserted in the cartridge holder 204, and a connector 208. The connector 208 and the cartridge holder 204 share a fastening means. In particular, the fastening means includes a first fastening feature 210 on the cartridge holder 204 and a second fastening feature 212 on the connector 208. The two fastening features 210, 212 may operate together to securely fasten the cartridge assembly 200 to the drug delivery device 202. As will be described in greater detail, if the connector 208 having the second fastening feature 212 is not attached to the cartridge holder 204, the cartridge holder 204 cannot connect to the drug delivery device 202. That is, the first fastening feature 210 of the cartridge holder 204 by itself is insufficient to properly attach the cartridge holder 204 to the drug delivery device 202. In a sense, the first fastening feature 210 by itself is an incomplete fastening means.

Fastening features 210 and 212 together form a set of fastening features. This embodiment depicted in FIG. 2 depicts one set of fastening features around the circumference of the cartridge assembly 200. However, more than one set of fastening features may be disposed around the circumference of the cartridge assembly 200. For example, cartridge assembly 300 depicted in FIG. 3 includes two sets of fastening features, and cartridge assembly 400 in FIG. 4 includes three sets of fastening features. Additional sets of fastening features are possible as well. It should be understood that the number of fastening features will depend on the corresponding fastening features of the device for which the assembly is intended to be connected with.

A connector having shared fastening means may be attached to the cartridge in a variety of ways. Generally, the connector can be attached to the cartridge in any way now known in the art or in any way later developed. The connector may be securely fitted around a sidewall of the drug cartridge. Further, the connector may be connected to the cartridge by adhesive and/or glue. Other examples include snap-fit features between the adaptor and cartridge. Alternatively, as discussed above, in some embodiments the fastening features are formed on the drug cartridge itself, rather than a connector that is attached to the drug cartridge.

In this alternative embodiment, the fastening features may be formed as part of the cartridge, for example, during molding.

When the connector is attached to the cartridge, the connector/cartridge may then be connected to the cartridge holder. The connector/cartridge may be connected to the cartridge holder in various ways. Further, as discussed above, the connector may be coded to the holder, so that a given connector(s) may only connect to a given cartridge(s) and vice versa.

In an example, the connector may connect to the cartridge holder by the meshing of various protrusions and indentations. The connector may be prevented from rotating relative to the holder by the meshing of various protrusions and indentations. For example, with reference to FIG. 2, when connector 208 is attached to cartridge holder 204, protrusion 214 of the connector 208 may mesh with indentation 216 of the cartridge holder 204.

Further, these various protrusions and indentation may provide coding so that only intended connectors can match with given cartridge holders and vice versa. For example, if the protrusion 214 has a larger circumferential extent than the circumferential extent of indentation 216, the protrusion 214 may not be able to connect to the cartridge holder 204.

Different coding features are also possible (e.g., more extensive coding features with additional protrusions/indentations). For instance, FIG. 3 depicts a connector 306 that has a plurality of protrusions that act as connecting features and coding features. FIG. 3 depicts an exemplary cartridge assembly 300 that is connectable to a drug delivery device (not depicted). Cartridge assembly 300 includes a cartridge holder 302, a cartridge 304 inserted in the cartridge holder 302, and a connector 306.

In this example, the cartridge assembly 300 comprises two sets of fastening features. As depicted, the cartridge holder 302 has fastening features 310, 312, and connector 306 has fastening features 314, 316. Further, cartridge holder 302 has a plurality of indentations 318, 320, 322. Connector 306 has a plurality of corresponding protrusions 324, 326, and 328. When the connector 306 is attached to the cartridge holder 302, protrusion 324 meshes with indentation 318, protrusion 326 meshes with indentation 320, and protrusion 328 meshes with indentation 322. A similar set of indentations and protrusions may be provided at another point along the circumference of the cartridge assembly 300, such as near fastening features 312 and 316, for example. Further, the connector 306 includes a non-rotation feature 330 that meshes with indentation 332. The non-rotation feature 330 prevents relative rotation between the cartridge holder 302 and the connector 306. The protrusions 324, 326, 328 also may act as non-rotation features to prevent relative rotation between the cartridge holder 302 and the connector 306. In other cartridge assemblies, the number, shape, and/or location of the indentations and protrusions may be varied to code given connectors to given cartridge holders.

FIG. 4 depicts another example of a cartridge assembly having shared fastening means. In this example, cartridge assembly 400 includes three sets of fastening features around the circumference of the assembly. FIG. 4 depicts an exemplary cartridge assembly 400 that is connectable to a drug delivery device (not depicted). Cartridge assembly 400 includes a cartridge holder 402, a cartridge 404 inserted in the cartridge holder 402, and a connector 406. The connector 406 and the cartridge holder 402 share a fastening means for fastening to a drug delivery device. The shared fastening means include three sets of shared fastening features. The first set of shared fastening features is formed by fastening features 408 of the cartridge holder 402 and fastening features 410 of the connector 406; the second set of shared fastening features is formed by fastening features 412 of the cartridge holder 402 and fastening features 414 of the connector 406; the third set of shared fastening features is formed by fastening features 416 of the connector 406 and corresponding fastening features of the cartridge holder 402. The protrusions forming the fastening features 410 mesh with indentation 418 of the cartridge holder 402, and the other protrusions of the connector 406 also mesh with other indentations (not shown) of the cartridge holder 402.

When the cartridge assembly with the shared fastening means between the holder and the connector (or cartridge itself) is assembled, the cartridge assembly may be connected to a drug delivery device. The connection of the cartridge assembly to the drug delivery device is described with reference to FIGS. 5-8. Generally, it will be seen that in order for a holder that shares its fastening means with a connector (or cartridge itself) to connect to a device, the holder is attached to the connector (or cartridge itself). Otherwise, the fastening means of the holder may not be a complete fastening means, and the design of the corresponding fastening means of the device may prevent the holder alone from connecting to the device because of the incomplete fastening means of the holder.

FIGS. 5-8 depict the connection of the cartridge assembly 200 of FIG. 2 to drug delivery device 202 of FIG. 2, which may comprise a dose setting mechanism. It should be understood, however, that the connection of the cartridge assemblies 300 and 400 may operate in the same or similar fashion.

Figure 6A:
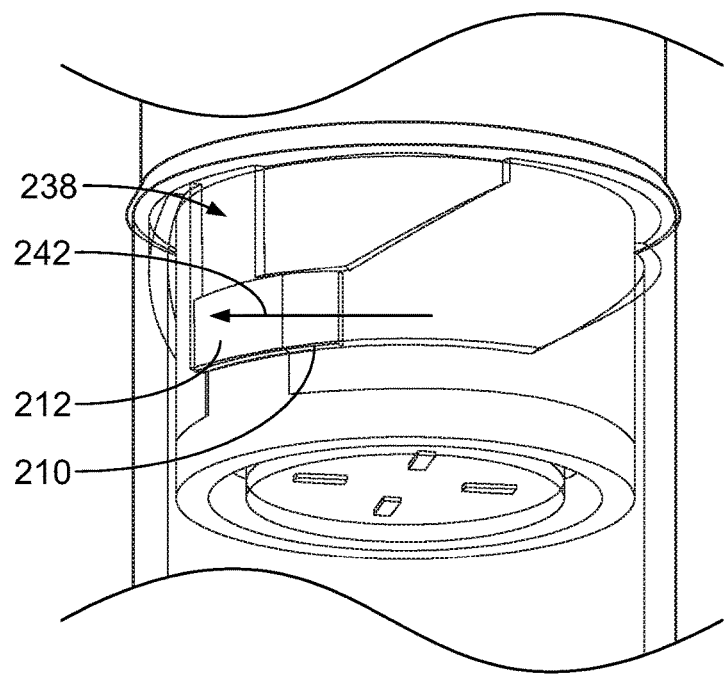
FIG. 6a is a perspective view of the exemplary cartridge assembly of FIG. 2 connected to the exemplary device of FIG. 2.
Figure 6B:
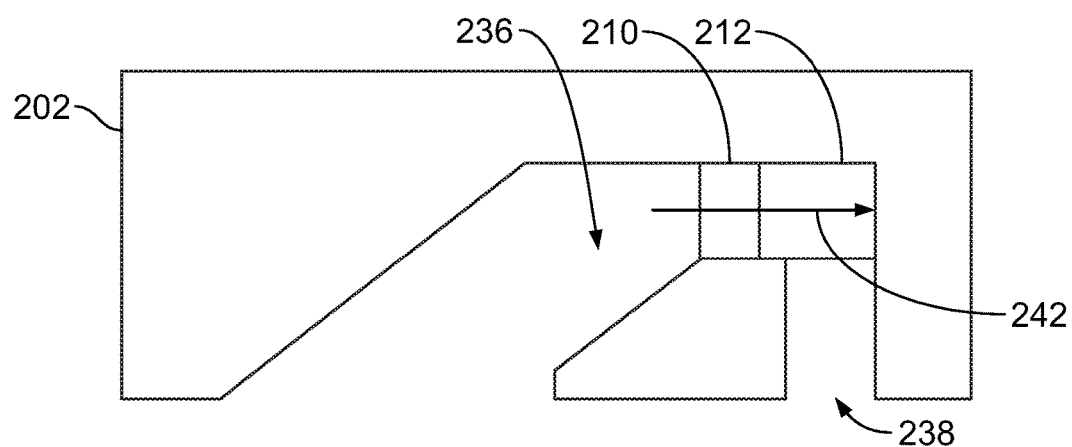
FIG. 6b is a 2D projection around the circumference of the exemplary device and exemplary cartridge assembly.
Figure 7:
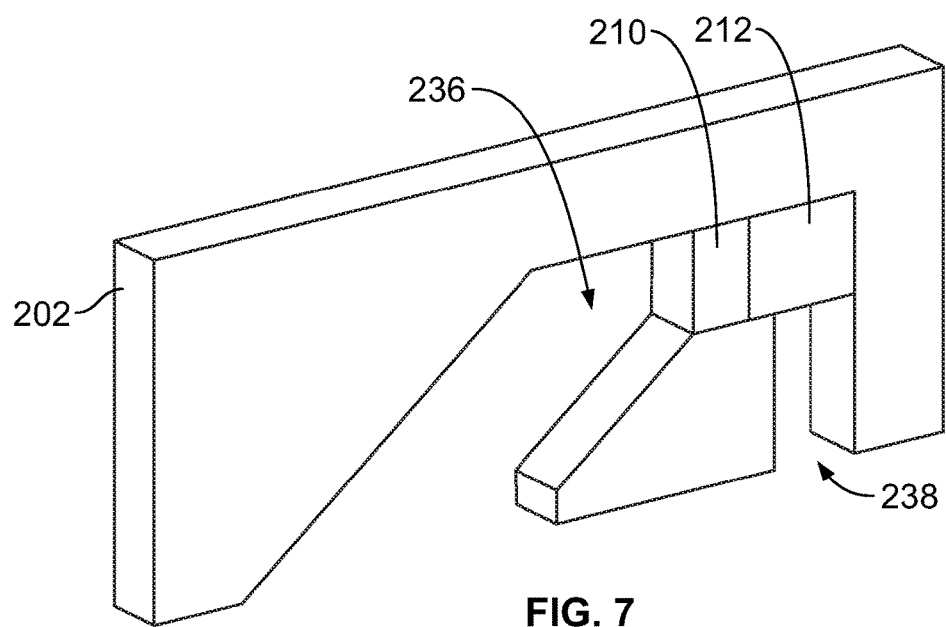
FIG. 7 is a perspective view of the 2D projection of FIG. 6b.

Specifically, FIGS. 5-7 illustrate when cartridge assembly 200 including connector 208 is attached to drug delivery device 202, and FIG. 8 illustrates when the cartridge assembly 200 not including the connector 208 is attached to the drug delivery device 202.

Figure 15:
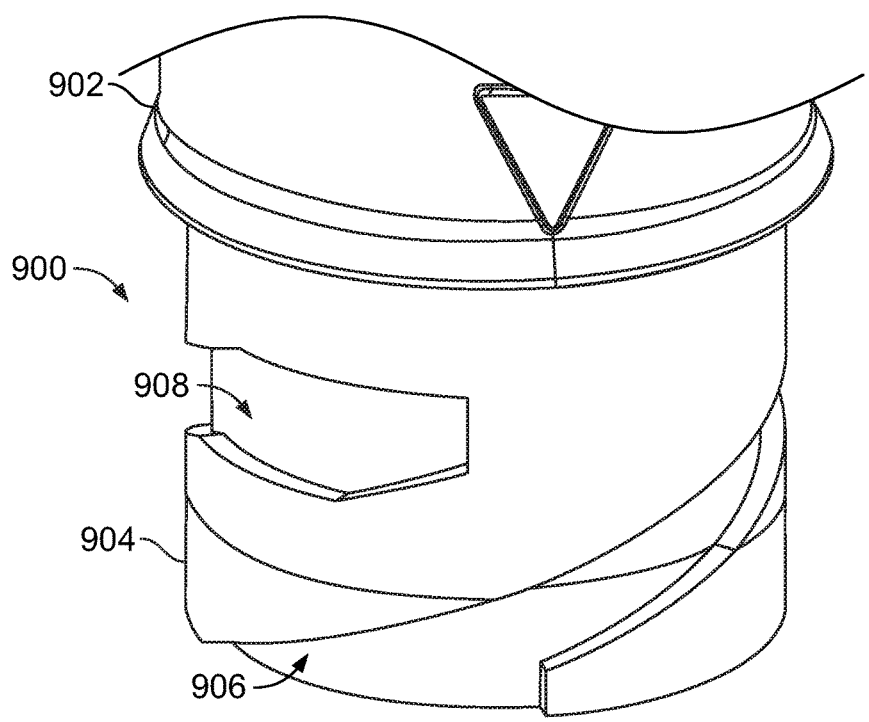
FIG. 15 is a perspective view of an exemplary cartridge holder and an exemplary connector having a shared fastening means.

As described above, the cartridge assembly 200 includes a shared fastening means that is shared between the cartridge holder 204 and the connector 208. Device 202 includes a corresponding fastening means. In this example, the fastening means of the cartridge assembly 200 and corresponding fastening means of drug delivery device 202 are a pin-and-groove-type fastening mechanism. Specifically, the shared fastening means of the cartridge assembly 200 forms the pin (e.g., first fastening feature 210 and second fastening feature 212 act as the pin) and the corresponding fastening means of the drug delivery device 202 comprises a groove 230. However, the corresponding fastening means and the shared fastening means of the assembly may take a variety of forms. For example, both pins could be on the device. As another example, one or more of the pins could be on the cartridge assembly, and the remainder of the pins could be on the device. As yet another example, fastening means other than a pin and groove can be used. As still yet another example, the fastening means shared between the connector and the cartridge holder could be the groove, and the drug delivery device may include the pin that interacts with the groove. An example cartridge holder and connector that include a shared fastening means, where the fastening means is a groove, is shown in FIG. 15. FIG. 15 depicts the proximal end of cartridge assembly 900, which includes cartridge holder 902 and connector 904. The connector 904, as discussed above, may be fitted on the drug reservoir or cartridge that is held within the cartridge holder 902.

As can be seen, the cartridge holder 902 and connector 904 share a fastening means, where the fastener comprises a groove. In particular, connector 904 includes a first portion 906 of the groove and cartridge holder 902 includes a second portion 908 of the groove. Together, first portion 906 and second portion 908 form a fastener. If a given connector (e.g., a connector attached to a given drug) is not intended to be used with a given cartridge holder, coding features may ensure that the two parts (e.g., parts 906 and 908) of the fastening means will not align with one another. If the two parts of the fastening means are not aligned, the cartridge assembly 900 will be unable to connect to a drug delivery device.

Returning to the example depicted in FIGS. 5-8, this groove 230 creates a path that a shared fastening feature of a cartridge assembly 200 travels along when the cartridge assembly 200 is inserted into the drug delivery device 202. Specifically, groove 230 includes an axial path portion 232, a helical path portion 234, and a rotational path portion 236. Groove 230 also includes an exit path portion or ejection channel 238. This exit path portion or ejection channel 238 may also be referred to as an "exit channel". When the connector 208 is missing from the cartridge assembly 200, the cartridge holder 204 over-rotates. When the cartridge holder 204 over-rotates, the incomplete fastening feature of the cartridge holder 204 will follow this ejection channel 238, and the cartridge assembly 200 will then be released from the drug delivery device 202.

Although the illustrated fastening means is a pin in a groove with axial, then helical, then rotational travel, it should be understood that the proposed concept may be used with any fastening means and any combination of directions in the travel.

Figure 5A:
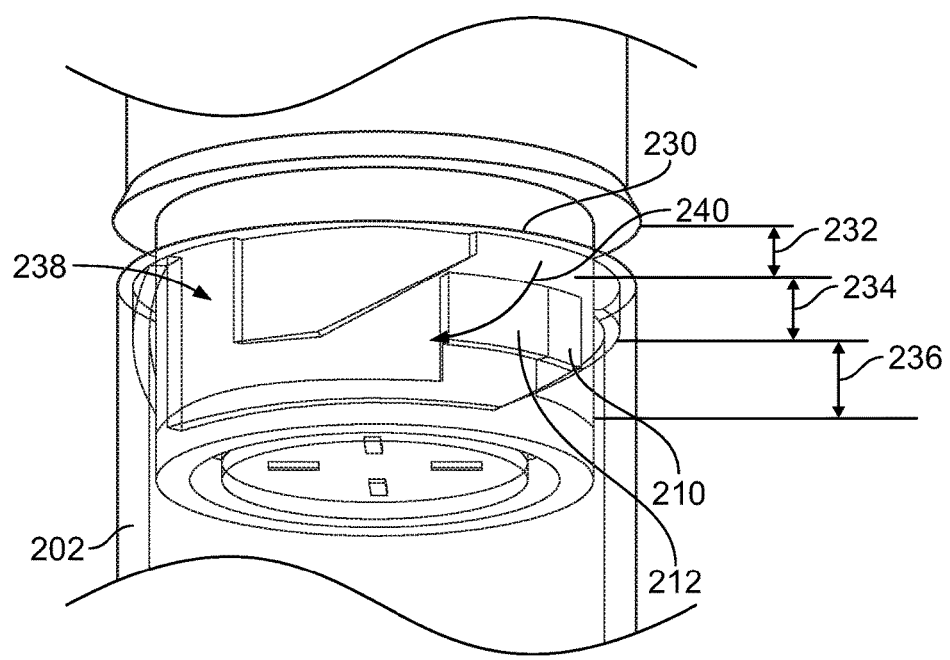
FIG. 5a is a perspective view of the exemplary cartridge assembly of FIG. 2 connected to the exemplary drug delivery device of FIG. 2.
Figure 5B:
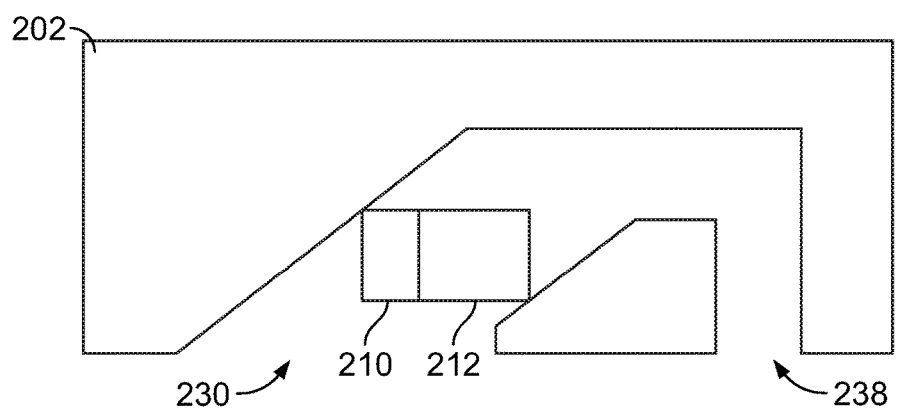
FIG. 5b is a 2D projection around the circumference of the exemplary device and exemplary cartridge assembly.

FIG. 5a depicts when cartridge assembly 200 is initially inserted into the drug delivery device 202, and FIG. 5b illustrates a 2D projection around the circumference of the cartridge assembly 200 and drug delivery device 202. The shared fastening means defined by fastening features 210, 212 is on a path defined by arrow 240. In this Figure, the fastening features are moving along the helical path portion 234 of groove 230.

FIG. 6a depicts when cartridge assembly 200 is fully fastened to the drug delivery device 202, and FIG. 6b illustrates a 2D projection around the circumference of the cartridge assembly 200 and drug delivery device 202. Further, FIG. 7 depicts another view of the projection around the circumference of the cartridge assembly 200 and drug delivery device 202 when the drug delivery device is fully fastened. In these Figures, the shared fastening means has traveled further along groove 230. Specifically, the fastening means travel on the rotational path portion 236 defined by arrow 242. The second fastening feature 212 is secured at the end of rotational path portion 236.

This second fastening feature 212 stops or prevents the first fastening feature 210 from entering the ejection channel 238. Therefore, the second fastening feature 212 may herein be referred to as a "stop feature." Further, the second fastening feature 212 is greater than the width of the ejection channel 238, and therefore the second fastening feature 212 cannot enter the ejection channel 238.

Figure 8A:
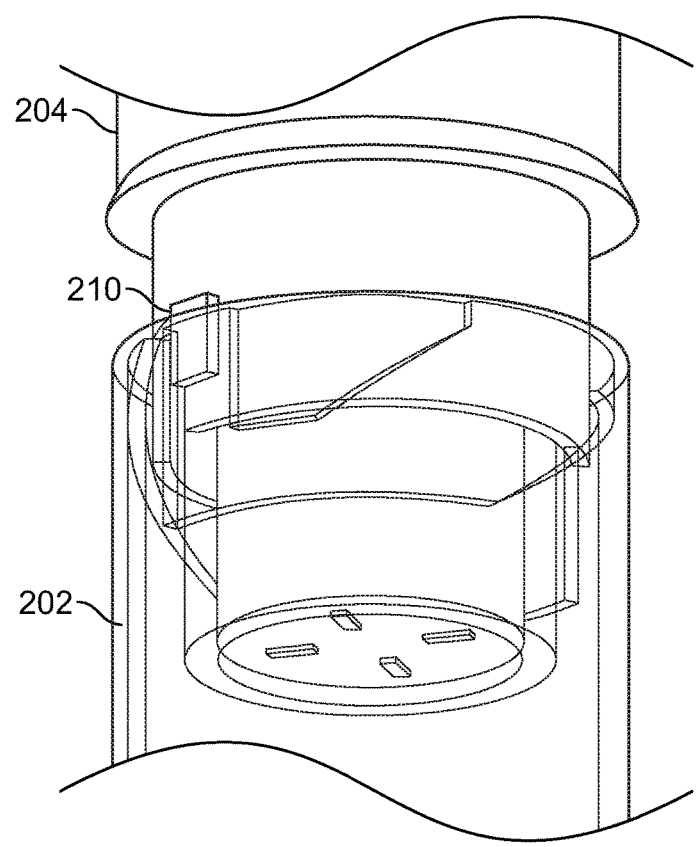
FIG. 8a is a perspective view of the exemplary cartridge holder of FIG. 2 connecting to the exemplary device of FIG. 2, where the holder is not attached to the exemplary connector.
Figure 8B:
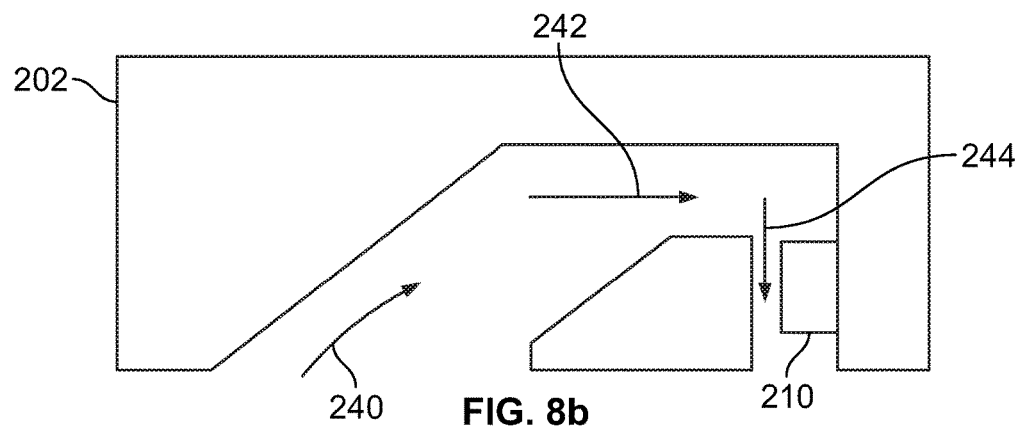
FIG. 8b is a 2D projection around the circumference of the exemplary device and exemplary cartridge holder.
Figure 9A:
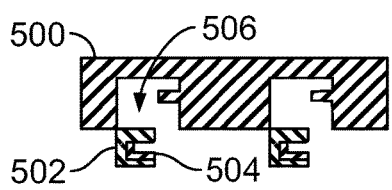
FIGS. 9-12 are 2D projections around the circumference of exemplary cartridge assemblies and devices.
Figure 9B:
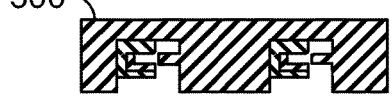
Figure 9C:
Figure 9D:
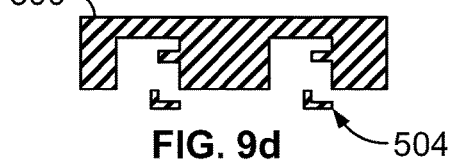

FIG. 8a depicts when cartridge assembly 200 without connector 208 is inserted into the drug delivery device 202, and FIG. 8b illustrates a 2D projection around the circumference of the cartridge assembly 200 and drug delivery device 202. Since connector 208 is not connected to the cartridge holder 204, the fastening means is not complete. Specifically, the cartridge holder 204 comprises the first fastening feature 210 but the cartridge assembly 200 is lacking the second fastening feature 212.

The fastening feature travels along the paths defined by arrows 240 and 242; however, since the cartridge holder 204 is not connected to the connector 208, there is no stop feature to prevent the first fastening feature 210 from over-rotating and entering the ejection channel 238. When the first fastening feature 210 enters the ejection channel 238, the fastening feature travels along the path defined by arrow 244. The first fastening feature 210 alone is an incomplete fastening means, because a complete fastening means should have a width greater than that of the ejection channel 238. Because the first fastening feature 210 exits through the ejection channel 238, a user will not be able to securely fasten that cartridge holder 204 to the drug delivery device 202.

As mentioned above, FIGS. 5-8 depict one example of a cartridge assembly 200 having a shared fastening means, where the cartridge assembly 200 is connectable to a drug delivery device 202. Other examples of shared fastening means of a cartridge holder and a connector and a corresponding fastening means of a device are depicted in FIGS. 9-13. Other examples in accordance with the proposed concept are possible as well.

Generally, these FIGS. 9-13 depict examples of different types of fastening means (e.g., different arrangement of grooves and different shapes and arrangements of the shared fastening features). Further, these Figures depict connection of an assembly to a device (i) when the cartridge assembly includes a connector with the shared fastening means and (ii) when the cartridge assembly does not include the connector.

FIG. 9 depicts a drug delivery device 500 and shared fastening features 502 and 504 of a cartridge holder and connector. The corresponding fastening feature of the drug delivery device 500 is groove 506. The groove 506 defines a path of axial travel, then rotational travel. FIGS. 9a-c depict various stages of the cartridge assembly fastening to the drug delivery device 500. FIG. 9d depicts when the cartridge holder alone (i.e., without the connector) is attached to the drug delivery device 500. As shown in FIG. 9d, the cartridge holder cannot be securely fastened to the drug delivery device 500 when the fastening features 502 of the connector are not present.

Figure 10A:
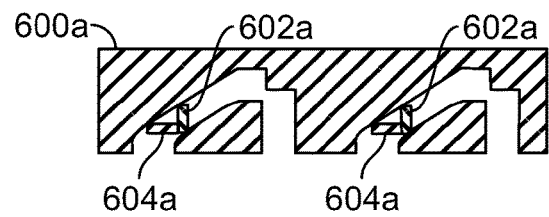
Figure 10B:
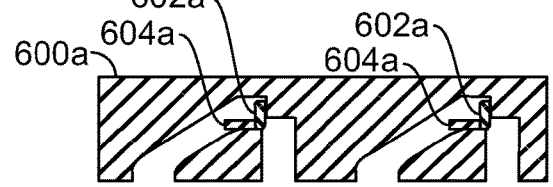
Figure 10C:
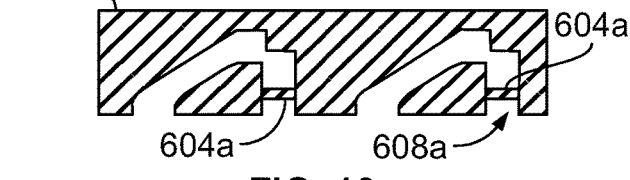
Figure 11A:
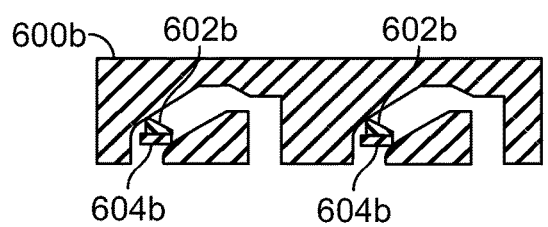
Figure 12A:
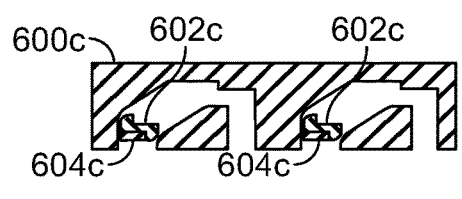
Figure 11B:
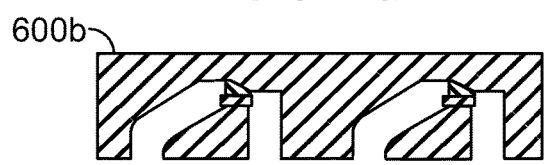
Figure 12B:
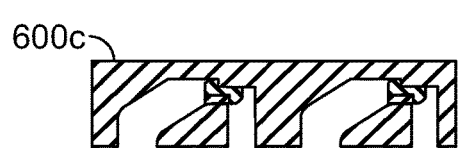
Figure 11C:
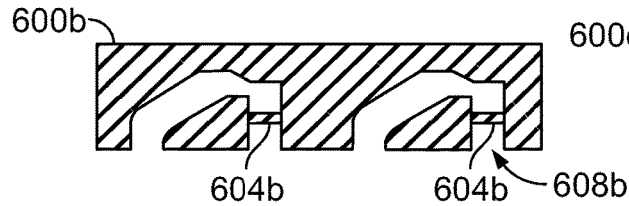
Figure 12C:
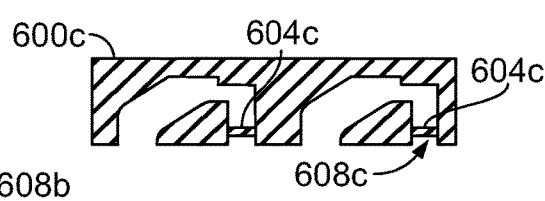

FIGS. 10-12 depict additional examples. Specifically, FIGS. 10a-b, 11a-b, and 12a-b depict various stages of a cartridge assembly fastening to a drug delivery device 600a/b/c, where the cartridge assembly includes a connector having the shared fastening means 602a/b/c. FIGS. 10c, 11c, and 12c depict the respective cartridge assemblies where the cartridge assemblies comprise only the cartridge holder and do not include a connector. As can be seen in each Figure, when the cartridge assembly does not have the appropriate connector with the shared fastening means, the fastening feature 604a/b/c on the cartridge holder will exit through the ejection channel 608a/b/c.

Figure 13A:
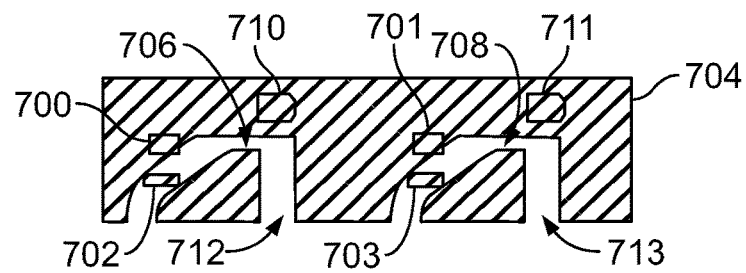
FIG. 13a-c are 2D projections around the circumference of an exemplary cartridge assembly connecting to an exemplary drug delivery device.

In some embodiments, the fastening feature on the connector (e.g., the stop feature) is not aligned with the fastening feature on the cartridge holder. In such an embodiment, coding may be achieved by the size or position of this stop feature, so that the fastening means (e.g., pin and groove) can be a standard feature. FIGS. 13a-d depict 2D projections around the circumference of an example cartridge assembly and an example drug delivery device 704. FIG. 13a depicts when a cartridge assembly having fastening features 700-703 is inserted into drug delivery device 704. Fastening features 700 and 701 are stop features that are disposed on a connector of the cartridge assembly, and fastening features 702 and 703 are the fastening means disposed on the cartridge holder. With reference to the first set of fastening features 700, 702, the fastening feature 700 on the connector is not aligned with the fastening feature 702 on the holder. Rather, the fastening feature 700 is located above fastening feature 702.

Drug delivery device 704 includes a corresponding fastening means for each set of fastening features 700, 702; 701, 703 on the cartridge assembly. These corresponding fastening means are grooves 706 and 708. Further, the drug delivery device 704 includes corresponding stop features 710 and 711. The stop features 710, 711 are located above grooves 706 and 708. As can be seen, since the fastening features 700, 702; 701, 703 on the connector and the cartridge holder are not aligned, the fastening feature 700, 701 on the connector does not need to travel through the groove 706, 708 on the drug delivery device 704.

Figure 13B:
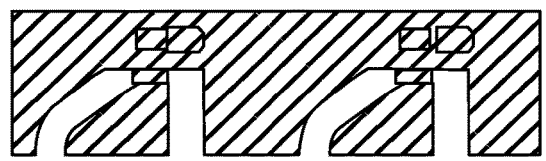

FIG. 13b depicts when the cartridge assembly is fully fastened to the drug delivery device 704. As can be seen, stop feature 710 acts to prevent fastening feature 700 from further movement, and stop feature 711 acts to prevent fastening feature 701 from further movement. Therefore, fastening features 702 and 703 are prevented from advancing to the ejection channels 712 and 713, respectively. FIG. 13d depicts another view of fastening feature 700 and stop feature 710 interacting with one another.

Figure 13C:
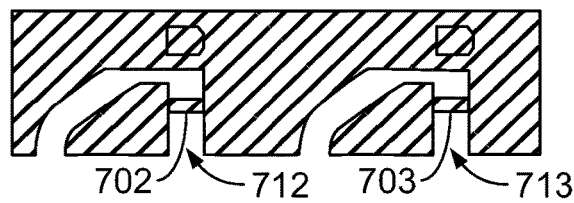
Figure 13D:
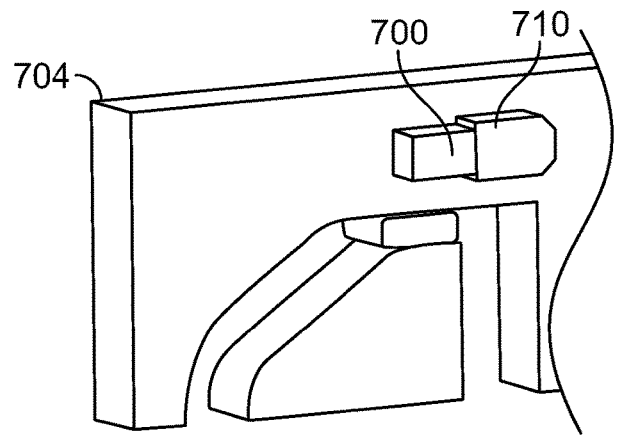
FIG. 13d is a perspective view of the 2D projection of FIGS. 13a-c.

FIG. 13c depicts when a cartridge assembly without the connector having part of the shared fastening means (i.e., the stop feature) is connected to the device. Because fastening features 700 and 701 are not present, the fastening features 702 and 703 over-rotate and travel into the ejection channels 712 and 713.

Beneficially, the location of the fastening means (i.e., stop feature) on the connector relative to the fastening means (i.e., the fastening pin) on the cartridge holder can be used to code the cartridge to the device. For example, a connector or cartridge having a stop feature that is located in the wrong position (e.g., a few mm above or below the corresponding stop feature of the device) would not operate to stop the pin, and thus the pin could then possibly exit through the ejection channel.

In certain embodiments a spring mechanism could help to ensure that the cartridge assembly is rejected if a connector having the shared fastening means is not fitted to the holder. In an example, the spring mechanism would be housed in the device, and when it contacts the proximal end of the cartridge it may apply a torque on the cartridge to bias it towards the ejection channel. If the shared fastening means is fitted, the second fastening feature 212, for instance, would prevent travel down the ejection channel. However, if the shared fastening means is not present (e.g., due to an incorrect cartridge assembly), the cartridge would move toward the ejection channel. Alternatively, or in addition to a torque, the spring mechanism may apply a distally directed force to urge an incorrect cartridge assembly out of the ejection channel or back out along the helical path portion.

Figure 16:
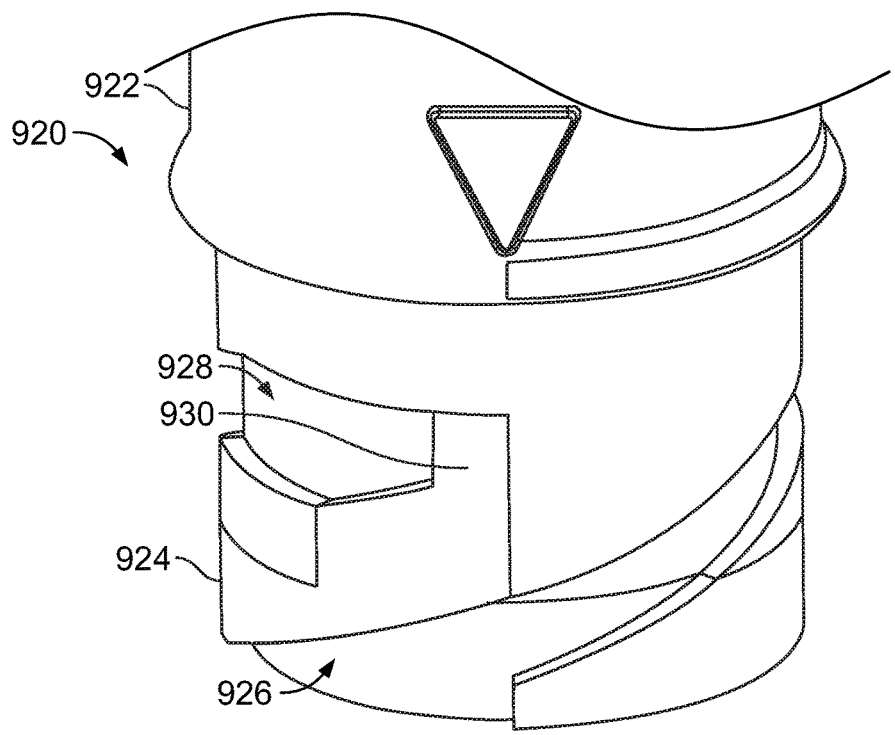
FIG. 16 is a perspective view of an exemplary cartridge holder and an exemplary connector having a shared fastening means.

In the embodiments described with reference to FIGS. 2-4, if the groove is on the cartridge assembly 200, 300, 400, the connector 208, 306, 406 can block the end of the groove to prevent over-travel. For example, FIG. 16 depicts a connector 924 that can block the end of the groove to prevent over-travel. Specifically, FIG. 16 depicts the proximal end of cartridge assembly 920, which includes cartridge holder 922 and connector 924. As can be seen, the cartridge holder 922 and connector 924 share a fastening means, where the fastening means is a groove. In particular, connector 924 includes a first portion 926 of the groove and cartridge holder 922 includes a second portion 928 of the groove. Together, first portion 926 and second portion 928 form the complete fastening means. Connector 924 further includes end stop 930. As seen in FIG. 16, end stop 930 blocks the end of the second portion 928 of the groove. When a cartridge not having a connector attached or not having a correct connector attached (e.g., a cartridge with a connector attached, but where the connector does not include an end stop) is placed in cartridge holder 922, the cartridge assembly 920 will not be able to be secured to a drug delivery device. In such a situation, since the cartridge assembly 920 will not include an end stop 930, the cartridge assembly 920 would rotate too far when being attached to a device. Thus, the cartridge assembly 920 will be unable to secure to the drug delivery device.

Additionally, the fastening means illustrated in FIGS. 15 and 16 may be coded to a drug delivery device or drug delivery devices in various ways. For example, the position of the end-stop features between the holder and connector may vary. Other ways of coding the fastening means to a drug delivery device or drug delivery devices are possible as well. Since the fastening means of the cartridge assembly may be coded in these various ways, only drug delivery devices having the correct corresponding fastening means will be able to connect to the coded cartridge assemblies.

A connector in accordance with this disclosure may have various circumferential extents. For example, the connector may have any circumferential extent ranging from 1 degree to 360 degrees. The examples shown above depict connectors that have a full circumferential extent of 360 degrees. However, it should be appreciated that connectors having a circumferential extent of fewer degrees is possible.

In given embodiments, the connector may or may not include a shoulder to locate over the proximal (i.e., open) end of the cartridge. In FIG. 3, the proximal end of the connector 306 has a shoulder inwardly directed from the outside diameter of the cartridge 304 towards the inner diameter of the cartridge 304. Such a shoulder may help to locate the connector 306 in an axial direction relative to the cartridge 304.

Further, in given embodiments, the connector may include features (e.g., cams) to activate the dispensing mechanism. Such an embodiment beneficially may provide additional coding, as a dosing mechanism may require cam features in order to activate. Therefore, a device may require the correct connector having the correct cams to dispense a dose. FIG. 4 shows an example connector 406 having cam features. Specifically, connector 406 has cam features 420 and 422.

Still further, in certain embodiments, retention features may clip the cartridge to the holder whilst still enabling easy removal, e.g. interference fit, snap fit, bayonet. For example, FIG. 9 shows a bayonet arrangement between the connector and cartridge holder.

Figure 14:
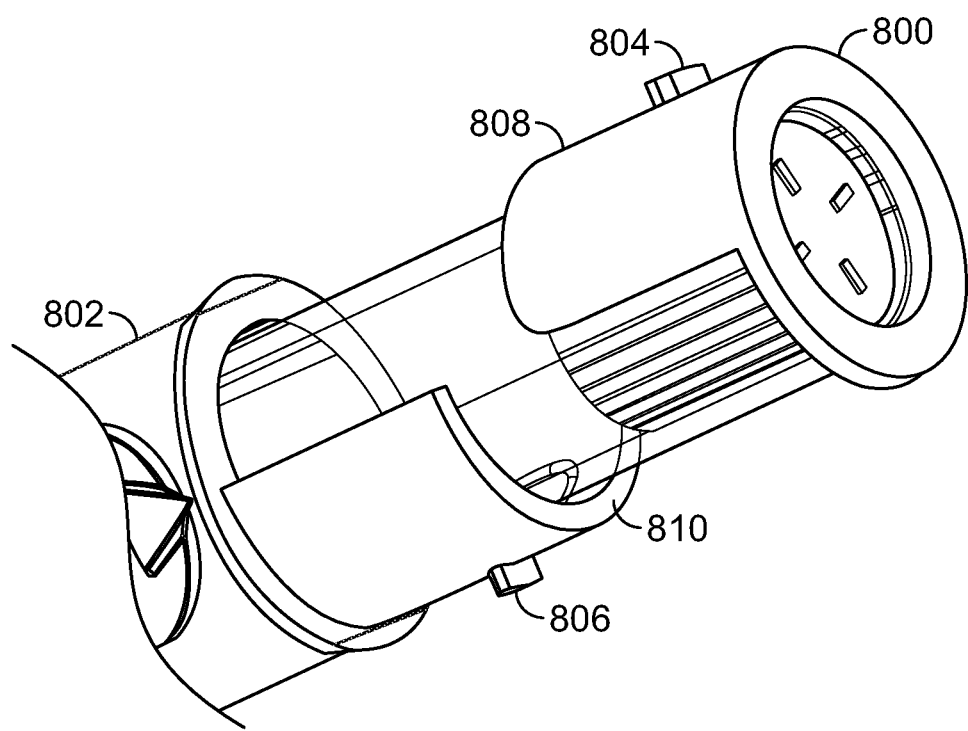
FIG. 14 is a perspective view of an exemplary cartridge assembly.

FIG. 14 depicts an additional method to share the fastening means between a cartridge holder and a connector. Connector 800 includes a shared fastening means. This is a simplified method to share fastening means. In this example, the connector 800 and the cartridge holder 802 are designed so that when connected, the connector 800 will cover a partial extent of the circumference of the cartridge assembly. If the connector 800 is not fitted to the cartridge holder 802, the cartridge holder 802 will not lock into the drug delivery device.

This simplified method for sharing a fastening means is similar to the examples described above, and thus will not be described in as great of detail. It should be explicitly noted, however, that many possibilities and permutations described above with respect to FIGS. 2-3 may equally apply to this cartridge assembly.

The cartridge assembly of FIG. 14 includes connector 800 and cartridge holder 802. The connector 800 and cartridge holder 802 share a fastening means for fastening to a drug delivery device. As seen in FIG. 14, the cartridge holder 802 includes a first fastening feature 806, and the connector 800 includes a second fastening feature 804. Both of the fastening features are needed in order to form a complete fastening means for connecting to an intended drug delivery device.

The connector 800 also has sidewall 808. Sidewall 808 only covers a partial extent of the circumference of the connector 800. In this example, the sidewall 808 only covers 180 degrees of the circumference. The protrusion forming the second fastening feature 804 is disposed on this sidewall 808.

Similarly, cartridge holder 802 includes a second sidewall 810. Second sidewall 810 only covers a partial extent of the circumference of the cartridge holder 802. In this example, the second sidewall 810 only covers 180 degrees of the circumference. The protrusion forming the first fastening feature 806 is disposed on this second sidewall 810.

When the connector 800 and the cartridge holder 802 are attached, the connector 800 and the cartridge holder 802 together form a substantially complete ring around a circumference of a cross-section of the cartridge holder 802 and connector 800. That is, the first sidewall 808 of the connector 800 and the second sidewall 810 of the cartridge holder 802 combine to form a complete (or substantially complete) circumference.

In this example as show in FIG. 14, half of the ring is on the cartridge holder 802 and half of the ring is on the connector 800. However, in order to code different drugs, the segments (i.e., sidewalls 808, 810) could be split at different angles and/or the connector 800 could be different lengths. In other words, the connector 800 may be coded to a given cartridge holder 802 or given cartridge holders 802 by the angle of the first sidewall 808 of the connector 800.

In the example of FIG. 14, the pin-type protrusion forming the second fastening feature 804 on the connector 800 is at approximately 180 degrees from the pin-type protrusion forming the first fastening feature 806 on the cartridge holder 802. When fastened to a device, the pin-type protrusions forming the first and second fastening features 804, 806 will follow grooves on the device.

In another embodiment, the pin on the cartridge holder may be narrower than the pin of the connector, so as to provide a stop feature similar to the stop feature in embodiments discussed above. In this case, if the cartridge holder is fastened without the connector, it will rotate too far, and the pin will follow the ejection channel. In yet another embodiment, the connector may be designed to contain part of the fastening groove, similar to the connectors illustrated in FIGS. 15 and 16.

The proposed shared fastening means may apply to drug delivery devices used with insulin, for instance, or with other drugs. The invention may apply to various devices, including an injector pen with a cartridge (e.g. 3 ml cylindrical glass cartridge) and a separate cartridge holder.

The proposed shared fastening means results in a number of advantages. For example, the proposed shared fastening means operates to ensure that an assembly may only be connected to a given device if the assembly has a proper connector. Moreover, there are quite a large number of different coding configurations between the holder and the connector and between the assembly and the drug delivery device that may be used. Consequently, with proposed shared fastening means and coding schemes, a large number of medicaments can be distinguished from one another. In addition, with the shared fastening means schemes, if a user attempts to load an incorrect cartridge assembly into a dose setting mechanism designed for a different cartridge assembly, the user may be alerted at an early stage of the assembly process. Further, in some embodiments, the cartridge can be gripped by the holder, thereby eliminating free-play, which may improve dose accuracy. If the cartridge is free to float axially in the cartridge holder, then the delivered dose might not be constant for a given advancement of the piston rod of the dose setting member, due to compliance of the stopper and septum. Thus, the holder gripping the cartridge may improve dose accuracy.

As another example, by having shared fastening means between a holder and a drug cartridge or connector, one may be unable to use an uncoded cartridge with a given drug delivery device. Preventing users from using uncoded cartridges may lead to enhanced safety because users will be unable to use uncoded cartridges with drug delivery devices that are not intended for the given uncoded cartridges. As yet another example, the drug container or cartridge can be coded directly to the drug delivery device, rather than a holder. Accordingly, in such an example, it is not necessary to code the cartridge to holder and to code the holder to device.

Exemplary embodiments of the present invention have been described. However, as those of skill in the art will recognize certain changes or modifications to such arrangements may be made. Those skilled in the art will understand, however, that further changes, modifications, revisions and/ or additions may be made to the presently disclosed arrangements without departing from the true scope and spirit of the present invention, which is defined by the claims.

REFERENCE NUMERALS 100 drug delivery device
102 dose setting member
103 distal end
104 cartridge holder
105 proximal end
106 removable cap
108 distal end of the cartridge holder
109 piston rod
111 cartridge holder cavity
117 dose setter
119 cartridge
121 thread
122 barrel
123 annular bead
125 medicament
126 neck
127 opening
128 stopper
130 distal end
131 shoulder
132 proximal end
133 seal or septum
134 diameter $D_1$
136 diameter $D_2$
200 cartridge assembly
202 drug delivery device
204 cartridge holder
206 cartridge
208 connector 210 first fastening feature
212 second fastening feature
214 protrusion
216 indentation
230 groove
232 axial path portion
234 helical path portion
236 rotational path portion
238 ejection channel
240 arrow
242 arrow
244 arrow
300 cartridge assembly
302 cartridge holder
304 cartridge
306 connector
310 fastening feature
312 fastening feature
314 fastening feature
316 fastening feature
318 indentation
320 indentation
322 indentation
324 protrusion
326 protrusion
328 protrusion
330 non-rotation feature
332 indentation
400 cartridge assembly
402 cartridge holder
404 cartridge
406 connector
408 fastening feature
410 fastening feature
412 fastening feature
414 fastening feature
416 fastening feature
418 indentation
420 cam feature
422 cam feature
500 drug delivery device
502 fastening feature
504 fastening feature
506 groove
600a/b/c drug delivery device
602a/b/c fastening feature
604a/b/c fastening feature
608a/b/c ejection channel
700 fastening feature
701 fastening feature
702 fastening feature
703 fastening feature
704 drug delivery device
706 groove
708 groove
710 stop feature
711 stop feature
712 ejection channel
713 ejection channel
800 connector
802 cartridge holder
804 second fastening feature
806 first fastening feature
808 first sidewall
810 second sidewall
900 cartridge assembly
902 cartridge holder
904 connector
906 first portion of the groove
908 second portion of the groove
920 cartridge assembly
922 cartridge holder
924 connector
926 first portion of the groove
928 second portion of the groove
930 end stop

The invention claimed is:

1. A cartridge assembly comprising:
a cartridge holder with a cavity,
a cartridge held in the cavity of the cartridge holder,
the cartridge holder being provided with a first fastening feature; and
a connector that is attached to the cartridge as a separate element or component, wherein a second fastening feature is provided on the connector in order to attach the cartridge to the cartridge holder,
wherein the first and second fastening features are provided to operate together as a shared first fastener to mount the cartridge assembly to a drug delivery device comprising a tubular housing having a second fastener to cooperate with the first shared fastener formed by the first and second fastening features, the first fastener being shared between the cartridge holder and the connector and wherein the connector is different from the cartridge, the cartridge holder and the drug delivery device.

2. The cartridge assembly of claim 1, wherein the connector allows the cartridge holder to be connected to the drug delivery device when the connector is attached to the cartridge holder.

3. The cartridge assembly of claim 1, wherein the connector is fitted around a sidewall of the cartridge.

4. The cartridge assembly of claim 1, wherein the connector is coded to the cartridge holder or wherein the first fastening feature and the second fastening feature are coded to the drug delivery device.

5. The cartridge assembly of claim 1, wherein the first fastening feature and the second fastening feature comprise at least two sets of fastening features.

6. The cartridge assembly of claim 1, wherein the first fastening feature of the cartridge holder by itself is insufficient to properly attach the cartridge holder to the drug delivery device.

7. The cartridge assembly of claim 1, wherein for a secure fastening of the cartridge assembly to the drug delivery device, the first fastening feature and the second fastening feature have to operate together.

8. The cartridge holder of claim 7, wherein for a secure fastening of the cartridge assembly to the drug delivery device both, the first fastening feature and the second fastening feature are required to engage with the second fastener of the drug delivery device.

* * * * *